(12) United States Patent
Schäfer et al.

(10) Patent No.: US 11,127,173 B2
(45) Date of Patent: Sep. 21, 2021

(54) SCALED RADIOGRAPHY RECONSTRUCTION

(71) Applicants: KONINKLIJKE PHILIPS N.V., Eindhoven (NL); ION BEAM APPLICATIONS S.A., Louvain-la-Neuve (BE)

(72) Inventors: Dirk Schäfer, Hamburg (DE); Peter George Van De Haar, Eindhoven (NL); Sebastien Brousmiche, Fouvain-la-Neuve (BE)

(73) Assignee: KONINKLIJKE PHILIPS N. V., Eindhoven (NL)

( * ) Notice: Subject to any disclaimer, the term of this patent is extended or adjusted under 35 U.S.C. 154(b) by 182 days.

(21) Appl. No.: 16/471,842

(22) PCT Filed: Dec. 20, 2017

(86) PCT No.: PCT/EP2017/083885
§ 371 (c)(1),
(2) Date: Jun. 20, 2019

(87) PCT Pub. No.: WO2018/115160
PCT Pub. Date: Jun. 28, 2018

(65) Prior Publication Data
US 2020/0090379 A1 Mar. 19, 2020

(30) Foreign Application Priority Data
Dec. 21, 2016 (EP) .................... 16205801

(51) Int. Cl.
*G06K 9/00* (2006.01)
*G06T 11/00* (2006.01)
(Continued)

(52) U.S. Cl.
CPC ............ *G06T 11/005* (2013.01); *A61B 6/032* (2013.01); *A61B 6/4258* (2013.01);
(Continued)

(58) Field of Classification Search
CPC ......... A61B 6/032; A61B 6/507; A61B 6/482; A61B 6/027; A61B 6/4014; A61B 6/4441;
(Continued)

(56) References Cited

U.S. PATENT DOCUMENTS

2004/0066909 A1* 4/2004 Lonn ...................... A61B 6/032
378/65
2006/0045235 A1 3/2006 Bruder
(Continued)

OTHER PUBLICATIONS

International Search Report/Written Opinion - PCT/EP2017/083885, dated Apr. 20, 2018.
(Continued)

*Primary Examiner* — Alex Kok S Liew
(74) *Attorney, Agent, or Firm* — Larry Liberchuk

(57) ABSTRACT

The invention relates to off-center detector 3D X-ray or proton radiography reconstruction. Redundancy weighting with a steep weighting function around the iso-axis typically leads to artifacts in the reconstruction, for example, if inconsistencies between two nominal redundant projections occur, e.g. due to slightly incorrect detector calibration or scatter correction, etc. With the present invention, an approach is presented for overcoming or mitigating these problems.

12 Claims, 2 Drawing Sheets

(51) Int. Cl.
  *A61B 6/03* (2006.01)
  *A61B 6/00* (2006.01)
  *G06T 3/40* (2006.01)
  *G06T 7/00* (2017.01)

(52) U.S. Cl.
  CPC ............ *A61B 6/5241* (2013.01); *A61B 6/585* (2013.01); *G06T 3/40* (2013.01); *G06T 7/0012* (2013.01); *G06T 2207/10116* (2013.01)

(58) Field of Classification Search
  CPC ..... A61B 6/5205; A61B 6/5258; A61B 6/504; A61B 6/481; A61B 6/037; A61B 6/583; A61B 6/484; G06T 11/006; G06T 2211/424; G06T 11/005; G06T 2207/10081; G06T 7/0012; G06T 5/002; G06T 11/008; G06T 15/08; G06T 2211/421; G06T 17/10; G06T 2200/04; G06T 2207/30096; G06T 5/005; G06T 5/30; G06T 7/11; G06T 7/155; G06T 7/62; G06T 2211/432; G06T 2207/30064; G06T 7/136
  See application file for complete search history.

(56) References Cited

U.S. PATENT DOCUMENTS

2009/0262997 A1* 10/2009 Zou ........................ A61B 6/583
  382/131
2012/0014582 A1 1/2012 Schaefer
2013/0004042 A1 1/2013 Yang
2015/0223766 A1* 8/2015 Besson .................. A61B 6/035
  378/5
2019/0064292 A1* 2/2019 Leghissa ............ G01R 33/4826

OTHER PUBLICATIONS

Schafer, Dirk et al "Cone-beam Filtered Back-Projection for Circular X-Ray Tomography with Off-Center Detector", 10TH International Meeting on Fully 3D Image Reconstruction in Radiology and Nuclear Medicine, Sep. 2009, pp. 86-89.

Min, Jonghwan et al "Analytic Image Reconstruction from Partial Data for a Single-Scan Cone-Beam Ct with Scattei Correction", Medical Physics, vol. 42, No. 11, Nov. 2015, pp. 6625-6640.

Nang, Ge "X-Ray Micro-Ct with a Displaced Detector Array", Medical Physics, vol. 29, No_ 7, Jul. 2002, pp_ 1634-1636.

* cited by examiner

SCALED RADIOGRAPHY RECONSTRUCTION

CROSS-REFERENCE TO PRIOR APPLICATIONS

This application is the U.S. National Phase application under 35 U.S.C. § 371 of International Application No. PCT/EP2017/083885, filed on Dec. 20, 2017, which claims the benefit of European Patent Application No. 16205801.0, filed on Dec. 21, 2016. These applications are hereby incorporated by reference herein.

FIELD OF THE INVENTION

The present invention relates to radiography reconstruction such as off-center detector 3D X-ray reconstruction or proton radiography reconstruction (in particular proton tomography reconstruction) and particularly to an apparatus or a method for off-center detector 3D X-ray reconstruction and to an apparatus or a method for proton radiography reconstruction.

BACKGROUND OF THE INVENTION

Off-center detector 3D X-ray reconstruction with, for example circular orbit, is used in a number of commercial available systems including Philips Brightview XCT and for imaging on radiation therapy systems from Elekta and IBA (e.g. IBA compact and 360° gantries) or C-arm systems (Siemens). Similarly, rather than using X-rays, other examples include PT radiography (in particular image stitching with different detector offsets at the same angle) or proton CT.

The projection data for the large field of view (LFOV) is obtained by rotating 360° with a fixed detector off-set or by two short scans (180° plus fan-angle) and shifting the detector from one side to the other.

Typically, in both cases a small detector overlap region (small in comparison to the detector size) is provided, where redundant data is measured. The detector overlap region contains redundant data for all cone angles in case of the two short scans and only for the central fan in case of 360° acquisition. In such case, one might consider rays with small cone angle as "quasi-redundant" or complementary.

However, due to a conventional redundancy weighting with a steep weighting function around the iso-axis prior to filtering, inconsistencies between two nominal redundant projections lead to artifacts in the reconstruction.

Even in approaches where typically less steep weighting functions are used, shutter penumbra or ghosting effects in an overlap region may lead to similar concerns. It may be noted here that the overlap size is one of the factors determining the size and strength of the artifacts. Size matters when it comes to hiding anatomical structures.

In the context of onboard systems for adaptive proton therapy, off-center detector configurations are of particular importance because an accurate evaluation of the full proton beam path inside the patient (from skin to isocenter) is considered mandatory. No truncation of the patient is therefore allowed. Moreover, off-center detector configuration artifacts appear at the proton isocenter where high soft-tissue detectability is desired and required. Any structured artifact could therefore be seen as an anatomical change or even hide potential changes leading to wrong patient positioning, diagnostic or selection of the best offline adaptive treatment option.

Similarly, off-center detector configurations can also be considered in proton radiography or proton CT. The same problems regarding inconsistencies between arcs or detector offsets at same gantry angles may occur.

SUMMARY OF THE INVENTION

It is an object of the present invention to provide an approach on the reconstruction in which the problem of the introduced artifacts is avoided or at least mitigated.

In a first aspect of the present invention an apparatus for off-center detector 3D X-ray reconstruction or for proton radiography reconstruction is presented, comprising a processing unit arranged for obtaining acquisition data measured by an off-center X-ray detector or by a proton detector, wherein the acquisition data includes a first portion and a second portion, wherein the first and second portion both cover at least a detector overlap region, determining a first reference value indicative of measured line integral values for the first portion in the detector overlap region and determining a second reference value of measured line integral values for the second portion in the detector overlap region, scaling at least one of the first portion and the second portion of the acquisition data based on a ratio of the first and second reference values, and performing reconstruction using the result of the scaling.

In a second aspect of the present invention a method for off-center detector 3D X-ray reconstruction or for proton radiography reconstruction is presented, comprising the steps of obtaining acquisition data measured by an off-center X-ray detector or by a proton detector, wherein the acquisition data includes a first portion and a second portion, wherein the first and second portion both cover at least a detector overlap region, determining a first reference value indicative of measured line integral values for the first portion in the detector overlap region and determining a second reference value of measured line integral values for the second portion in the detector overlap region, scaling at least one of the first portion and the second portion of the acquisition data based on the first and second reference values, and performing reconstruction using the result of the scaling.

It was realized by the inventors that inconsistencies between two nominal redundant projections may occur, e.g. due to slightly incorrect detector calibration or scatter correction, etc., while in the previous conventional approaches an ideal world was assumed in which (quasi-) redundant line integral data would indeed be completely identical. The present invention provides for a "forcing" of data to be equal, of which it is known that it should be equal.

While a similar scaling with a centered detector in a 360° case may have only limited impact on the image quality as such, artifacts from inconsistent calibration or projection processing between two arcs may nevertheless be addressed.

In an embodiment, the apparatus for proton radiography reconstruction further comprises the proton detector or an arrangement including the proton detector and a proton source.

In an embodiment the proton detector is arranged for performing multiple measurements with different offsets.

In another embodiment, the apparatus for off-center detector 3D X-ray reconstruction further comprises the off-center 3D X-ray detector or an arrangement including the X-ray detector and an X-ray source.

In an embodiment, only the second portion of the acquisition data is scaled with a ratio of the first reference value and the second reference value.

In an alternative embodiment, the first portion is scaled with a ratio of the first reference value and a base value and the second portion is scaled with a ratio of the base value and the second reference value.

One option to the scaling involves the scaling of only one of the involved portions, while leaving the other portion unchanged in this regard. However, it is also possible that there is scaling possibly to a differing degree for all portions involved.

It is furthermore possible that the planning CT can be used to retrieve ideal projections or rays at some specific angles where the base value is to be estimated, e.g. where the planning CT can be used (by forward projection).

In a further embodiment for proton radiography reconstruction the first portion is scaled with a ratio of the first reference value and a first base value obtained by forward projection of a planning CT of a first arc and the second portion is scaled with a ratio of a second base value corresponding to the first base value recomputed for angles of a second arc and the second reference value.

In a preferred embodiment, the acquisition data is obtained in a course of a rotation of 360° with a fixed detector off-set or by two scans of more than 180° and shifting the detector from one side to another side.

In a preferred embodiment, the performing of the reconstruction includes a redundancy weighting.

According to embodiments of the invention, the acquisition data is obtained by realizing an arbitrary trajectory around an examination object. Examples of such trajectories, include, among others, circular arcs, including circular arcs shorter than 180° +fan angle for tomosynthesis reconstruction, helical scanning schemes and iso-centric non-circular scanning of arbitrary trajectory length.

In a further aspect of the present invention a computer program or software product is presented for off-center detector 3D X-ray reconstruction, the software product comprising program code means for causing a computer to carry out the steps of the method of the present invention when the software product is run on the computer.

It shall be understood that the apparatus of claim 1, the method of claim 5, and the computer program of claim 12 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

In the context of the invention, it is proposed to use the (quasi-) redundant rays measured with different detector offset to force equality in a certain projection region to mitigate the artifacts produced by inconsistencies, as discussed above and explained with respect to embodiments as indicated below.

In a certain area in the region where (quasi-) redundant data are measured, the average (or an indicative value thereof) of the measured line integral values for each projection is logged.

In an embodiment, the pre-processing and back-projection of the first half of the complete acquisition is unchanged, while for the second half, the measured line integral on the region of interest is compared to that with the projection containing the (quasi-) redundant data. The measured line integral values of the second half acquisition are scaled with the ratio of the two line integral values.

Figure 1:
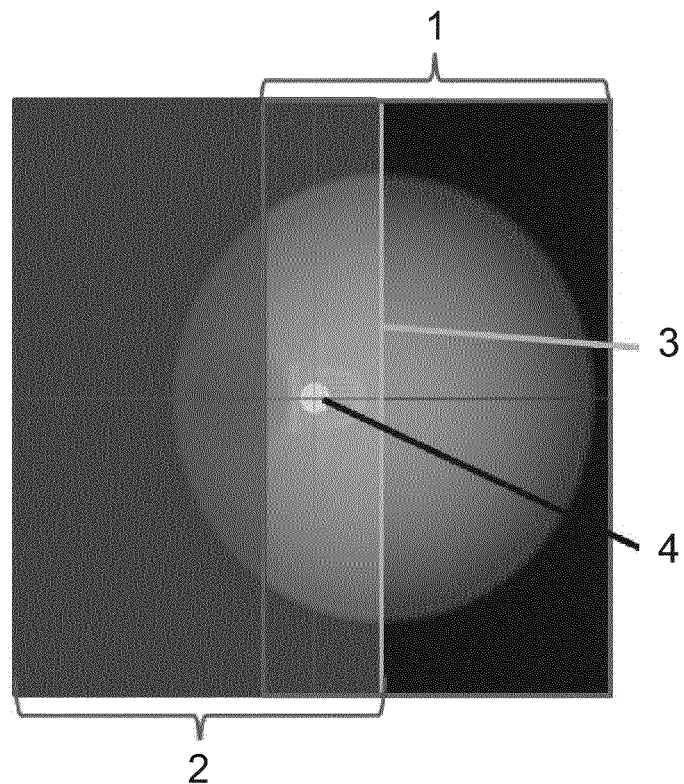
FIG. 1 shows an illustration of overlap and redundant data regions for short scan and 360° acquisitions.
Figure 2:
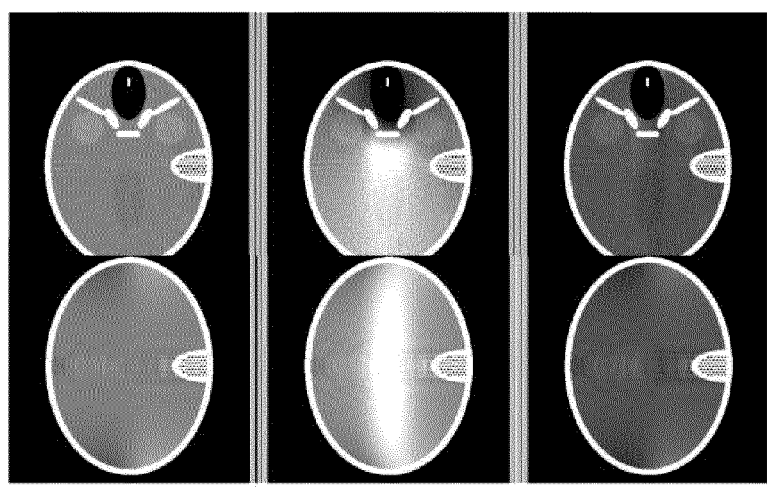
FIG. 2 shows a reconstruction result of conventional processing and of a processing according to the invention in comparison to a reference for a simulation with a drift of the magnitude of the line integral values of +/−5%.

The selection of areas of redundant data is illustrated in FIG. 1 and reconstruction results are shown in FIG. 2.

FIG. 1 shows an illustration of overlap and redundant data regions for short scan and 360° acquisitions.

The first portion 1 and the second portion 2 of the acquisition data overlap in a detector overlap region 3, while this depends on the size of the physical detector and the offset.

In case of two short scans, the detector overlap region 3 is used for calculating the line integral values.

In case of a 360° acquisition, there is a small(er) region 4 of quasi-redundant data, which may be used for calculating the line integral values.

FIG. 2 shows a reconstruction result of conventional processing and of a processing according to the invention in comparison to a reference for a simulation with a drift of the magnitude of the line integral values of +/−5%.

In the upper portion of FIG. 2, axial views of the reference (on the left), a conventional reconstruction (in the middle) and a reconstruction according to the invention (on the right) are shown, while the lower portions shows corresponding coronal views. The reconstructions results are for a +/−5% drift of magnitude in the line integral values for a 360° acquisition with a 40 mm detector overlap (L/W 30/150 HU, single slice).

Figure 3:
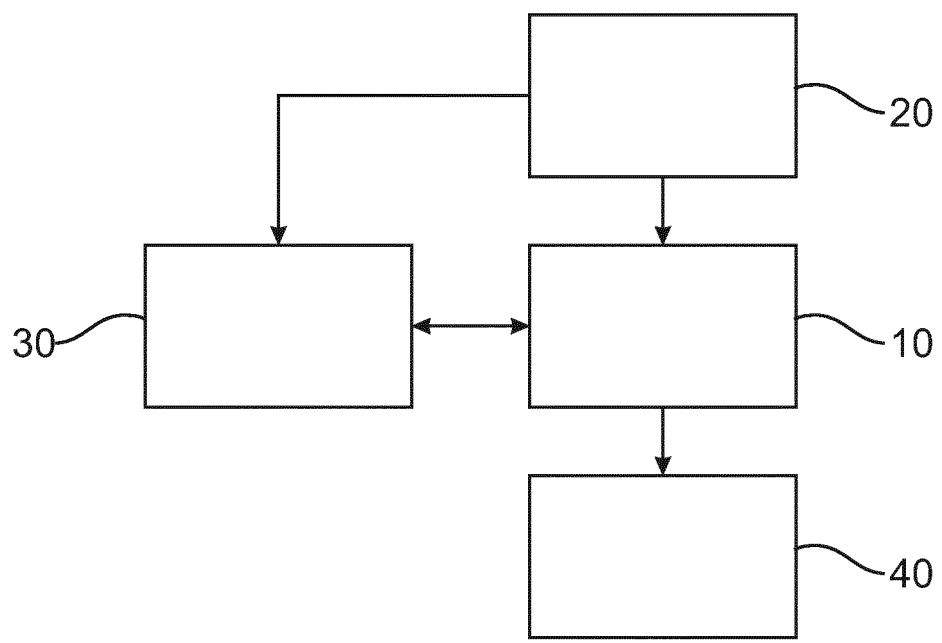
FIG. 3 shows schematically a system including an apparatus according to an embodiment of the invention.

FIG. 3 shows schematically a system including an apparatus 10 according to an embodiment of the invention.

The apparatus 10 for reconstruction is coupled to an off-center detector X-ray apparatus 20 and a memory 30, while the X-ray apparatus 20 and the memory 30 are also coupled.

The X-ray apparatus 20 is arranged to obtain the raw data of the measurement by carrying out the X-ray operation and may transfer the raw data (directly or after some preliminary processing) either to the reconstruction apparatus 10 or to the memory 30.

The apparatus 10 for reconstruction thus may obtain the data on which the reconstruction is based from the X-ray apparatus 20 or from the memory 30.

The apparatus 10 is arranged to perform the reconstruction according to the present invention and is furthermore arranged to forward the reconstruction data to a display 40 for display and/or to the memory 30 for storage (and later display).

Figure 4:
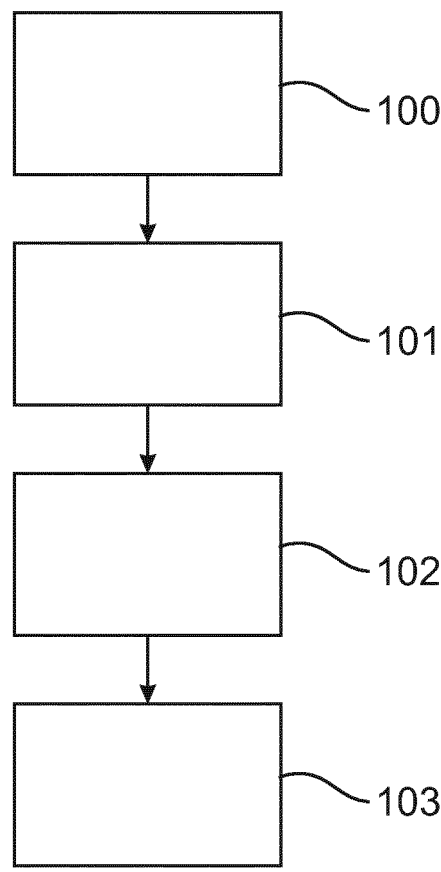
FIG. 4 shows a schematic flow diagram illustrating a method according to an embodiment of the invention.

FIG. 4 shows a schematic flow diagram illustrating a method according to an embodiment of the invention In an obtainment step 100 acquisition data is obtained, e.g. directly from an X-ray apparatus including an off-center X-ray detector (a concept with which the skilled person is well familiar, so that no further explanation is needed) or from a memory or the like in which such data is stored.

The acquisition data includes a first portion and a second portion, wherein the first and second portion both cover at least a detector overlap region, as it is illustrated in FIG. 1.

In a following determination step 101, a first reference value indicative of measured line integral values for the first portion in the detector overlap region is determined, while, in parallel or separately, also a second reference value of measured line integral values for the second portion in the detector overlap region is determined.

Based on the first and second reference values, in a scaling step 102 at least one of the first portion and the second portion of the acquisition are scaled.

Using the result of the scaling, in a reconstruction step 103, the reconstruction is performed, while this reconstruction process as such corresponds to the conventional approaches.

While the invention has been illustrated and described in detail in the drawings and foregoing description, such illustration and description are to be considered illustrative or exemplary and not restrictive; the invention is not limited to the disclosed embodiments.

The invention can, in particular, be used for or implemented in the context of C-arm systems, RT on-board imager, Spect/CT systems, etc.

Furthermore, while it is realized that the above discussion of exemplary embodiments refers to the case of an off-center 3D X-ray reconstruction, it will be appreciated by the skilled person that the above discussion similarly applies to, for example, PT radiography (image stitching with different detector offsets at same angle) or Proton CT.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like obtaining or acquiring data, determining or calculating values, scaling and performing reconstruction can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus for off-center detector 3D X-ray reconstruction or for proton radiography reconstruction, comprising a processing unit arranged for
    obtaining acquisition data measured by an off-center X-ray detector or by a proton detector, wherein the acquisition data includes a first portion and a second portion, wherein the first and second portion both cover at least a detector overlap region,
    determining a first reference value indicative of measured line integral values for the first portion in the detector overlap region and determining a second reference value of measured line integral values for the second portion in the detector overlap region,
    scaling at least one of the first portion and the second portion of the acquisition data based on a ratio of the first and second reference values, and
    performing reconstruction using the result of the scaling.

2. The apparatus for proton radiography reconstruction according to claim 1, further comprising the proton detector.

3. The apparatus according to claim 2, wherein the proton detector is arranged for performing multiple measurements with different offsets.

4. The apparatus for off-center detector 3D X-ray reconstruction according to claim 1, further comprising the off-center 3D X-ray detector.

5. A method for off-center detector 3D X-ray reconstruction or for proton radiography reconstruction, comprising the steps of
    obtaining acquisition data measured by an off-center X-ray detector or by a proton detector, wherein the acquisition data includes a first portion and a second portion, wherein the first and second portion both cover at least a detector overlap region,
    determining a first reference value indicative of measured line integral values for the first portion in the detector overlap region and determining a second reference value of measured line integral values for the second portion in the detector overlap region,
    scaling at least one of the first portion and the second portion of the acquisition data based on the first and second reference values, and
    performing reconstruction using the result of the scaling.

6. The method according to claim 5, wherein only the second portion of the acquisition data is scaled with a ratio of the first reference value and the second reference value.

7. The method according to claim 5, wherein the first portion is scaled with a ratio of the first reference value and a base value and the second portion is scaled with a ratio of the base value and the second reference value.

8. The method according to claim 5, wherein the first portion is scaled with a ratio of the first reference value and a first base value obtained by forward projection of a planning CT of a first arc and the second portion is scaled with a ratio of a second base value corresponding to the first base value recomputed for angles of a second arc and the second reference value.

9. The method for according to claim 5, wherein the acquisition data is obtained in a course of a rotation of 360° with a fixed detector off-set or by two scans of more than 180° and shifting the detector from one side to another side.

10. The method according to claim 5, wherein the performing of the reconstruction includes a redundancy weighting.

11. The method for according to claim 5, wherein the acquisition data is obtained by realizing an arbitrary trajectory around an examination object.

12. A software product stored on a non-transitory computer-readable medium for off-center detector 3D X-ray reconstruction or proton radiography reconstruction, the software product comprising program code means for causing a computer to carry out the steps of the method as claimed in claim 5 when the software product is run on the computer.

* * * * *